United States Patent
Bouchet et al.

(10) Patent No.: US 6,235,899 B1
(45) Date of Patent: May 22, 2001

(54) METHOD FOR PREPARING ALKYLOXY FURANONE DERIVATIVES, COMPOUNDS OBTAINED BY SAID METHOD AND USE OF SAID COMPOUNDS

(75) Inventors: Raphael Bouchet, Les Angles; Francis Brion, Balma; Colette Colladant, Rosny sous Bois; Jacques Lagouardat, Noisy le Grand., all of (FR)

(73) Assignee: Hoechst Marion Roussel (FR)

( * ) Notice: Subject to any disclaimer, the term of this patent is extended or adjusted under 35 U.S.C. 154(b) by 0 days.

(21) Appl. No.: 09/463,014

(22) PCT Filed: Jul. 9, 1998

(86) PCT No.: PCT/FR98/01480

§ 371 Date: Feb. 1, 2000

§ 102(e) Date: Feb. 1, 2000

(87) PCT Pub. No.: WO99/03852

PCT Pub. Date: Jan. 28, 1999

(30) Foreign Application Priority Data

Jul. 15, 1997 (FR) .................................. 97 08932

(51) Int. Cl.⁷ ........................ C07D 43/10; C07D 487/00; C07D 307/33
(52) U.S. Cl. ........................................... 540/500; 549/313
(58) Field of Search .............................. 549/313; 540/500

(56) References Cited

FOREIGN PATENT DOCUMENTS 9535308   12/1995   (WO) .
9722619    6/1997   (WO) .

OTHER PUBLICATIONS

Chapman, "Synthesis . . . Enzyme", Bioorganic & Medicinal Chemistry Letters, vol. 2, No. 6, pp. 613–618, 1992.
Feber et al, "Catalystic . . . Furanones", Tetrahedron, vol. 50, No. 16, pp. 4775–4794, 1994.
de Lange et al, "Asymmetric . . . Furanones", Tetrahedron, vol. 45, No. 21, pp. 6799–6818, 1989.
Feringa et al, "Asymmetric . . . Diols", Tetrahedron Letters, vol. 29, No. 11, pp. 1303–1306, 1988.

*Primary Examiner*—Bruck Kifle
(74) *Attorney, Agent, or Firm*—Biermann, Muserlian and Lucas

(57) ABSTRACT

The invention relates to a novel process for preparing compounds of the formula (IV) or (I):

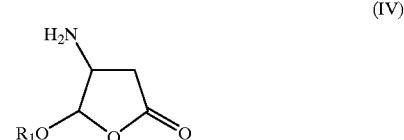

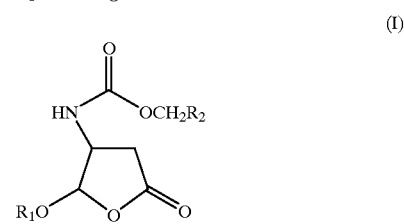

from the racemic alkoxyfuranone of the formula (II):

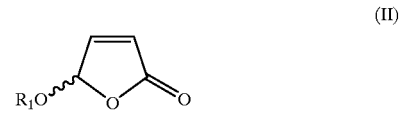

$R_1$ and $R_2$ being as defined in the description, to the novel compounds of the formula (IV) as well as to the intermediate compounds of this process, and to the use of the compounds of the formula (IV) or (I) in the process for the synthesis of compounds which inhibit interleukin-1beta converting enzyme.

17 Claims, No Drawings

METHOD FOR PREPARING ALKYLOXY FURANONE DERIVATIVES, COMPOUNDS OBTAINED BY SAID METHOD AND USE OF SAID COMPOUNDS

This application is a 371 of PCT/FR98/01480 filed Jul. 9, 1998.

The present invention relates to a novel process for preparing alkoxyfuranoneamine derivatives, to the compounds obtained by this process, and to the use of these compounds in the synthesis of inhibitors of interleukin-1beta converting enzyme.

Patent Applications WO 95/35308, WO 97/22619, WO 97/22618, EP 519 748 and WO 96/33209 describe compounds which inhibit interleukin-1beta converting enzyme.

The process for preparing some of the compounds described in the patent applications mentioned above uses the compounds of the formula (I) below:

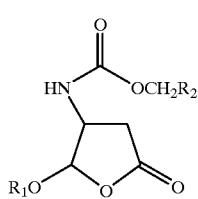

(I)

in which $R_1$ represents an ethyl radical and $R_2$ represents a $-CH=CH_2$ radical.

The compounds of the formula (I) are prepared from protected L-aspartic acid and require 4 synthetic steps: 1) acylation, 2) reduction, 3) oxidation, 4) cyclization, (Chapman K. T. et al., Bioorg. Med. Chem. Lett. 2(6), 613–8 (1992)).

This process has major drawbacks, in particular when it is desired to obtain chiral compounds of the formula (I). More specifically, an expensive chiral starting reagent, β-tert-butyl L-aspartate, has to be used, and above all chromatographic methods have to be used to isolate and/or purify the various diastereoisomers.

One object of the present invention is thus to find another route for the synthesis of the compounds of the formula (I) which avoids the use of this starting material and which does not require chromatographic separations.

The Applicant thus proposes a novel synthetic route starting with the alkoxyfuranone of the formula (II) in racemic form, giving access to the novel compounds of the formulae (IVa), (IVb), (IVc) and (IVd) as defined below, in salified or non-salified form, which are then protected, where necessary, in order in particular to obtain the compounds of the formula (I)

This process has the advantage of being able to be carried out on large scale, starting with a readily accessible and inexpensive compound of the formula (II), with the separation and/or purification steps being carried out by crystallization rather than by chromatography. Each diastereoisomer of the formula (III), (IV) or (I) can thus be isolated.

The present invention thus relates, on the one hand, to the compounds of the formula (IVa), (IVb), (IVc) or (IVd) below:

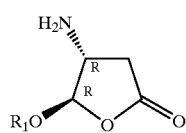

(IVa)

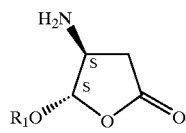

(IVb)

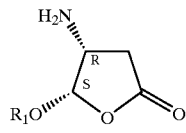

(IVc)

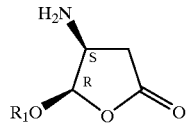

(IVd)

in which $R_1$ is an alkyl group containing from 1 to 4 carbon atoms or a phenylalkyl group containing from 7 to 11 carbon atoms, as well as the addition salts thereof with acids.

The invention naturally extends to the salts of the compounds of the formula (IVa), (IVb), (IVc) or (IVd), such as, for example, the salts formed with inorganic or organic acids on the amine. The acids may thus be hydrochloric, hydrobromic, nitric, sulphuric, phosphoric, acetic, formic, propionic, benzoic, maleic, fumaric, succinic, tartaric, citric, oxalic, glyoxylic or aspartic acid, alkanesulphonic acids such as methanesulphonic or ethanesulphonic acid, arylsulphonic acids, such as benzenesulphonic or paratoluenesulphonic acid, and arylcarboxylic acids.

They may also be chloroacetic or trichloroacetic acid. Most particularly, they are salts formed with hydrochloric acid.

When $R_1$ is an alkyl group containing from 1 to 4 carbon atoms, it can be, in particular, methyl, ethyl, butyl or propyl, and most particularly ethyl.

The term "phenylalkyl" preferably refers to the benzyl group.

The invention more particularly relates to the compound of the formula (IVd) as defined above, as well as the addition salts thereof with acids.

The invention most particularly relates to the compounds of the formula (IVd) in which $R_1$ is an ethyl group, as well as the addition salts thereof with acids.

Moreover, the present invention relates to a process for preparing compounds of (IVa), (IVb), (IVc) or (IVd) as described above, characterized in that it comprises at least one of the following steps:

a) action of an arylamine of the formula $R_3R_4$ $CHNH_2$, in which $R_3$ is a hydrogen atom or an alkyl group containing from 1 to 4 carbon atoms and $R_4$ is an optionally substituted aryl, on the racemic alkoxyfuranone of the formula (II):

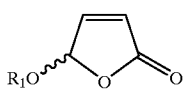

(II)

in which $R_1$ is an alkyl group containing from 1 to 4 carbon atoms or a phenylalkyl group containing from 7 to 11 carbon atoms,
and production of the trans isomer compounds (4R,5R) and (4S,5S) of the formulae (IIIa) and (IIIb) respectively:

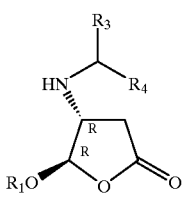

(IIIa)

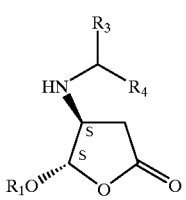

(IIIb)

which subsequently
are separated by crystallization, carrying out, if necessary, one or more salification reactions,
or, when $R_3$ is a hydrogen atom, are resolved by the action of an optically active acid,
b) where appropriate, epimerization reaction on the compound of the formula (IIIa) or (IIIb), in salified or non-salified form, in the presence of an acid, in order to obtain the cis isomer compounds (4R,5S) or (4S,5R) of the formula (IIIc) or (IIId), which are salified if necessary,

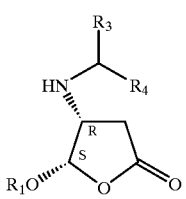

(IIIc)

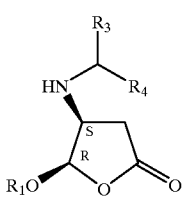

(IIId)

c) hydrogenolysis reaction,
either on the trans isomer (4R,5R) or (4S,5S) of the formula (IIIa) or (IIIb), in salified or non-salified form, in order to obtain the compound of the formula (IVa) or (IVb) in the form of the trans isomer (4R,5R) or (4S,5S) as defined above, which is then, if necessary, salified and/or protected, or on the cis isomer (4R,5S) or (4S,5R) of the formula (IIIc) or (IIId), in salified or non-salified form, in order to obtain the compound of the formula (IVc) or (IVd) in the form of the cis isomer (4R,5S) or (4S,5R), as defined above, which is, if necessary, salified and/or protected.

In particular, the reaction for protecting the amines of the formula (IVa), (IVb), (IVc) or (IVd), in salified or non-salified form, is carried out by the action of the chloroformate of the formula Cl—CO—O—CH$_2$—R$_2$, R$_2$ representing a tert-butyl, (C$_2$–C$_4$)-alkenyl, (C$_2$–C$_4$)-alkynyl or phenyl radical, which may be substituted or unsubstituted, in order to obtain the compounds of the formula (Ia), (Ib), (Ic) or (Id) respectively, in the form of the trans diastereoisomers (4R, 5R) and (4S,5S) or the cis diastereoisomers (4R,5S) and (4S,5R), which, if necessary, are salified,

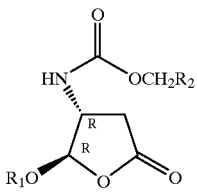

(Ia)

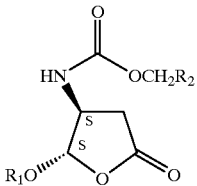

(Ib)

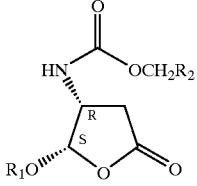

(Ic)

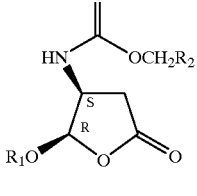

(Id)

The action of the arylamine $R_3R_4CHNH_2$ on the racemic alkoxyfuranone of the formula (II) is carried out according to the standard methods required for the Michael reaction, that is to say, in particular, in a dipolar aprotic solvent, such as dimethylformamide, at room temperature. The process can also be performed with the R or S phenylethylamine or in aqueous isopropanol.

The separation of the two trans isomers (4R,5R) and (4S,5S), i.e. the compounds of the formulae (IIIa) and (IIIb) respectively, by crystallization is carried out according to the methods known to those skilled in the art concerning the separation of isomers. As a preferred example, the separation is carried out by the action of trichloroacetic acid in a solvent such as tert-butyl methyl ether or aqueous isopropanol. The trans isomer (4R,5R) (IIIa) is crystallized in the form of the trichloroacetic acid salt, while the trans isomer (4S,5S) (IIIb) is recovered in the form of the monochloroacetic acid salt by treatment of the mother liquors in the presence of monochloroacetic acid.

When $R_3$ is a hydrogen atom (non-chiral amine), the separation (resolution) is then carried out by means of a chiral acid, such as tartaric acid, camphorsulphonic acid, salicylic acid, dibenzoyltartaric acid or $R^+2,4$-hydroxyphenoxypropionic acid.

The epimerization reaction on one of the isomers (4R,5R) or (4S,5S) of the formula (IIIa) or (IIIb) is carried out in the presence of a Lewis acid, such as ferric chloride or titanium tetrachloride, optionally complexed with tetrahydrofuran, boron trichloride, boron trifluoride etherate and tin tetrachloride, or of an organic acid, such as methanesulphonic acid, trifluoroacetic acid or para-toluenesulphonic acid. It is preferably tin tetrachloride, in the presence of a relatively non-polar solvent, such as dichloromethane, or methanesulphonic acid in a solvent, such as toluene.

The hydrogenolysis reaction on the cis or trans diastereoisomers of the formula (IIIa), (IIIb), (IIIc) or (IIId) is carried out according to the standard methods known to those skilled in the art, for example by the action of hydrogen in the presence of 10% palladium-on-charcoal in tetrahydrofuran.

The acylation reaction with the chloroformate is preferably carried out in the presence of a base, such as pyridine, in a relatively non-polar solvent, such as dichloromethane.

The formation of the base from the corresponding salt, i.e. the return to the free amine, and the methods of salification with the acids as defined above are carried out according to the methods known to those skilled in the art.

As regards the compounds of the formula (III), when $R_3$ is an alkyl group containing from 1 to 4 carbon atoms, it is preferably methyl or ethyl, and when $R_4$ is an aryl group, it is preferably phenyl or naphthyl.

As regards the compounds. of the formula (I), when $R_2$ is a ($C_2$–$C_4$) alkenyl or ($C_2$–$C_4$) alkynyl group, it is preferably —CH=CH$_2$, —C CH, —CH=CH$_2$—CH$_3$ or —C C—CH$_3$.

The protection reactions on the compounds of the formula (I) are carried out according to the methods known to those skilled in the art, and in particular with reference to the book by Philip J. Kociensky, Protecting Groups, Ed. Georg. Thieme Verlag, Stuttgart New-York, 1994.

The present invention more particularly relates to the process as defined above, characterized in that the separation, by crystallization, of the compounds of the formulae (IIIa) and (IIIb) is carried out:

a) by the action of trichloroacetic acid, in order to obtain the corresponding salt of the formula (IIIa) or (IIIb), b) followed by the action of monochloroacetic acid on the mother liquors, in order to obtain the salt corresponding to the other diastereoisomer of the formula (IIIa) or (IIIb).

The present invention most particularly relates to a process for preparing, as described above, the compounds of the formula (IVd) or (Id) as defined above, characterized in that it comprises at least one of the following steps:

a) action of the R phenylethylamine on the compound of the formula (II), in order to obtain the compounds of the formulae (III'a) and (III'b) below

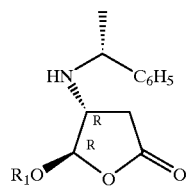

(III'a)

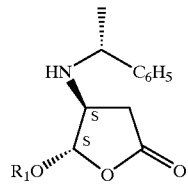

(III'b)

b) separation of trans stereoisomers of the formulae (III'a) and (III'b) by the action of trichloroacetic acid, in order to obtain the stereoisomer (III'b) (4S,5S) in the form of the trichloroacetic acid salt, followed by the action of monochloroacetic acid, in order to obtain the stereoisomer (III'a) (4R,5R) in the form of the monochloroacetic acid salt, c) where appropriate, return to the free amine by the action of a base, d) epimerization reaction on the stereoisomer (4S,5S) of the formula (III'b) in the presence of an acid, in order to obtain a cis stereoisomer (4S,5R) of the formula (III'd):

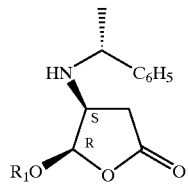

(III'd)

e) if necessary, crystallization after salification by the action of an acid, such as monochloroacetic acid or dichloroacetic acid, f) where appropriate, return to the free amine by the action of a base, g) if necessary, recrystallization after salification, in particular in the form of the hydrochloride, h) hydrogenolysis of the cis stereoisomer (4S,5R) of the formula (III'd), in order to obtain the compound of the formula (IVd) in the form of the cis diastereoisomer (4S,5R)

i) where appropriate, the action of allyl chloroformate on the compound of the formula (IVd), in order to obtain the compound of the formula (Id) in the form of the cis diastereoisomer (4S,5R), with $R_1$ representing —CH=CH$_2$.

The invention also relates most particularly to a process for preparing, as described above, compounds of the formula (IVd) or (Id) as defined above, characterized in that it comprises at least one of the following steps a) action of the S phenylethylamine on the compound of the formula (II), in order to obtain the compounds of the formulae (III"a) and (III"b) below:

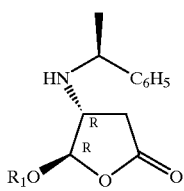

(III"a)

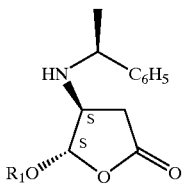

(III"b)

b) resolution of the trans stereoisomers of the formulae (III"a) and (III"b) by the action of trichloroacetic acid, in order to obtain the stereoisomer (III"a) (4R,5R) in the form of the trichloroacetic acid salt, followed by the action of monochloroacetic acid, in order to obtain the stereoisomer (III"b) (4S,5S) in the form of the monochloroacetic acid salt,
c) if necessary, return to the free amine by the action of a base,
d) epimerization reaction on the stereoisomer (4S,5S) of the formula (III"b) in the presence of an acid, in order to obtain a cis diastereoisomer (4S,5R) of the formula (III"d):

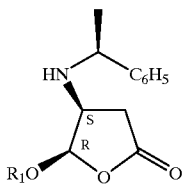

(III"d)

e) if necessary, crystallization after salification by the action of an acid, such as monochloroacetic acid or dichloroacetic acid,
f) where appropriate, return to the free amine by the action of a base,
g) if necessary, recrystallization after salification, in particular in the form of the hydrochloride,
h) hydrogenolysis of the cis stereoisomer (4S,5R) of the formula (III"d), in order to obtain the compound of the formula (IVd) in the form of the cis diastereoisomer (4S,5R)
i) where appropriate, the action of allyl chloroformate on the compound of the formula (IVd), in order to obtain the compound of the formula (Id) in the form of the cis diastereoisomer (4S,5R).

The invention most particularly relates to the process as defined above, characterized in that the addition of the amine to the compound of the formula (II) is carried out in dimethylformamide or in aqueous isopropanol.

The invention most particularly relates to the process as defined above, characterized in that the epimerization reaction is carried out with tin tetrachloride or methanesulphonic acid.

The invention most particularly relates to the process as defined above, characterized in that $R_1$ is an ethyl radical.

The invention most particularly relates to the process as defined above, characterized in that the separation of the trans stereoisomers with trichloroacetic acid (step b) is carried out in aqueous isopropanol.

The invention most particularly relates to the process using the (R) phenylethylamine, characterized in that the epimerization reaction on the stereoisomer (4S,5S) of the formula (III"b) (step d) is carried out in the presence of methanesulphonic acid in toluene.

The invention most particularly relates to the process using the (R) phenylethylamine, characterized in that the crystallization (step e) is carried out by the action of dichloroacetic acid in toluene.

The invention also relates to the use:

either of the compounds of the formula (IVa), (IVb), (IVc) or (IVd) as defined above or obtained from the process as described above, or of the compounds of the formula (Ia), (Ib), (Ic) or (Id) obtained from the process as described above, in amidation reactions, starting with the acid of the formula A—COOH, to give a compound of the formula (V) below:

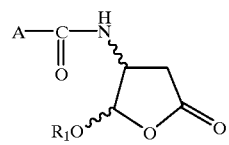

(V)

A representing any organic radical.

The invention also relates to the use:

either of the compounds of the formula (IVb) or (IVd) as defined above or obtained from the process as described above, or of the compounds of the formula (Ib) or (Id) obtained from the process as defined above, in the synthesis of the compounds of the formula (V), which have inhibitory activity on interleukin converting enzyme.

These compounds of the formula (V) are described in particular in the patent applications WO 95/35308, WO 97/22619, EP 0 519 748 and WO 96/33209.

The invention most particularly relates to the use:

either of the compound of the formula (IVd) in which $R_1$=ethyl, as defined above or obtained from the process as described above, or of the compound of the formula (Id) in which $R_1$=ethyl, obtained from the process as described above, in the preparation of a compound of the formula (V) which has inhibitory activity on interleukin converting enzyme.

A subject of the invention is, most particularly, the use:

either of the compound of the formula (IVd) in which $R_1$=ethyl, as defined above or obtained from the process as described above, or of the compound of the formula (Id) in which $R_1$=ethyl, obtained from the process as described above, in the preparation of the compound of the formula (V) with the following structure:

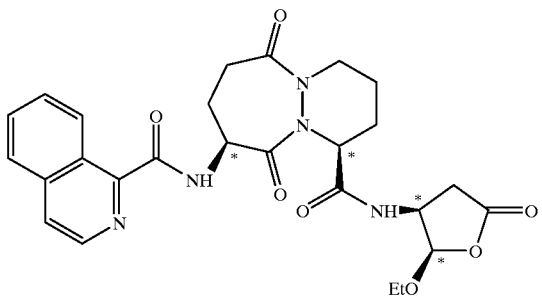

This compound is described in patent application WO 97/22619 (Pdt 412e).

The invention also relates to the compounds of the formulae (IIIa), (IIIb), (IIIc) and (IIId), as well as the addition salts with the acids as described above, as novel intermediate compounds, with the exception of the compounds of the formulae (III"a) and (III"b) in which $R_1$=methyl.

The compounds of the formula (II) are known or are readily accessible from the methoxyfuranone by the action of PTSA (para-toluenesulphonic acid), in the presence of water, and then of a reagent of the formula $(R_1Q)_3CH$ in the presence of an acid catalyst.

The examples which follow illustrate the invention without, however, limiting it.

EXAMPLE 1

(2R-cis) 2-propenyl (2-ethoxytetrahydro-5-oxo-3-furanyl) carbamate

Stage 1: Michael Addition

4(R*) dihydro-5-ethoxy-4-[(1-phenylethyl)amino]-2 (3H)-furanone 15 ml of 98% R-(+)-phenylethylamine are added over the course of 30 minutes at between 23 and 25° C., under an inert atmosphere, to 15 g of racemic ethoxyfuranone in 75 ml of dimethylformamide, and the solution obtained is stirred for 24 hours and then poured into a water/ice mixture. Isopropyl ether is added, and this mixture is extracted, washed, dried and evaporated under reduced pressure to give 27 g of an oil corresponding to the expected 50/50 mixture of the trans isomers.

NMR (CDCl$_3$; 250 MHz)

| | | |
|---|---|---|
| 1.12; 1.22 | (t) | CH$_2$CH$_3$ |
| 1.37 | (dd) | CH$_3$ (—NH—CH(CH$_3$) (Ph)) |
| 2.13 | (dd, J = 3.5 and 17.5) | |
| 2.35 | (dd, J= 3 and 17.5) | CH$_2$ at 3 of the furanone. |
| 2.70 | (dd, J = 7.5 and 17.5) | |
| 2.80 | (dd, J = 7 and 17.5) | |
| 3.26 | (m) | CH at 4 of the furanone |
| 3.30 to 3.90 | (m) | CH$_2$CH$_3$ |
| 3.82 | (m) | CH (—NH—CH(CH$_3$) (Ph)) |
| 5.00 | (d, J = 1.5) and 5.32 (d, J = 1.5) | CH at 5 of the furanone |
| 7.2 to 7.4 | (m) | 5H aromatic |

Stage 2: Resolution of the Two Trans Diastereoisomers

A) production of the trans diastereoisomer (4S,5S)

4(S)[4α(S*), 5β]-dihydro-5-ethoxy-4-[(1-phenylethyl)amino]-2(3H)-furanone trichloroacetate A solution of 10.6 g of trichloroacetic acid (99,5%) in 50 ml of tert-butyl methyl ether is added over 20 min. to 27 g of the mixture of diastereoisomers obtained in the above stage in 164 ml of tert-butyl methyl ether. The solution obtained is stirred for 2 hours at 20–25° C. and then for 2 hours at 0–5° C. 12 g of the (4S,5S) isomer are obtained in the form of the trichloroacetic acid salt.

[α$_D$]=+71° (c=1% CH$_3$OH)

NMR (CDCl$_3$ ; 250 MHz)

| | | |
|---|---|---|
| 1.15 | (t) | CH$_2$CH$_3$ |
| 1.75 | (d, J = 0 7) | CH$_3$ (—NH—CH(CH$_3$) (Ph)) |
| 2.78 | (dd, J = 8.5 and 18.5) | |
| 3.05 | (dd, J = 4 and 18.5) | CH$_2$ at 3 of the furanone. |
| 3.43 | (ddd,J = 2–4 and 8.5) | CH at 4 of the furanone |
| 3.59 | (dq, 1H) 3.79 (dq 1H) | CH$_2$CH$_3$ |
| 4.29 | (q,J = 7)) | (—NH—CH(CH$_3$) (Ph)) |
| 5.77 | (d,J = 1,5) | CH at 5 of the furanone |
| 7.42 to 7.57 | | 5H aromatic |
| 9.80 | (broad) | H mobile |

B) production of the trans diastereoisomer (4R,5R)

4(R)[4α(R*),5β]-dihydro-5-ethoxy-4-[(1-phenylethyl)amino]-2(3H)-furanone chloroacetate The mother liquors from the above stage are washed with saturated sodium bicarbonate solution and then with water, after which they are re-extracted once with isopropyl ether. After drying, the solution is evaporated under reduced pressure to give 15.45 g of the expected product in the form of an oil. 5 g of monochloroacetic acid are added to the 15.45 g of product in 130 ml of isopropanol, and this mixture is heated to 40° C. Dissolution and then crystallization are observed, after which the mixture is stirred for 1 hour at room temperature and then for 2 hours at 0–5° C. 11.98 g of the expected (4R,5R) isomer are obtained in the form of the monochloroacetic acid salt.

Stage 3: Production of the Desalified (4S,5S) Compound

4(S)[4α(S*),5β]-dihydro-5-ethoxy-4-[(1-phenylethyl)amino]-2(3H)-furanone 11.8 g of the salt obtained in Stage 2A and 120 ml of dichloromethane are mixed together at room temperature, followed by addition of 100 ml of saturated sodium bicarbonate solution. After stirring for 10 min., the mixture is extracted, washed, dried and evaporated under reduced pressure to give 7.1 g of the desalified product.

[α=$_D$]=+114° (c=1% CH$_3$OH)

Stage 4: Epimerization: Production of the (4S,5R) Diastereoisomer

4(S)[4α(S*),5α]-dihydro-5-ethoxy-4-[(1-phenylethyl)amino]-2(3H)-furanone 28.6 ml of 1M tin tetrachloride in dichloromethane are added, under an inert atmosphere over 1 hour at 4±1° C., to 6.8 g of the desalified (4S,5S) compound obtained in Stage 3 in 135 ml of dichloromethane, and the mixture is stirred for 40 minutes at this temperature. 11 ml of acetic acid are then added, the mixture is stirred for 30 minutes at 5° C., poured into a water/ice mixture and washed, cyclohexane is added, this mixture is brought to pH 7–8 by addition of sodium bicarbonate, and it is then extracted with cyclohexane, dried and evaporated under reduced pressure to give 4.39 g of the expected product in the form of an oil corresponding to a cis/trans ratio of 90/10.

[α$_D$]=−1°5 (c=1% CH$_3$OH)

NMR (CDCl$_3$ ; 250 MHz)

| | | |
|---|---|---|
| 1.23 | (t) | CH$_2$CH$_3$ |
| 1.40 | (d, J = 6.5) | CH$_3$ (—NH—CH(CH$_3$) (Ph)) |
| 2.39 | (dd, J = 11 and 17) | |
| 2.61 | (dd, J = 8 and 17) | CH$_2$ at 3 of the furanone. |
| 3.32 | (m) | CH at 4 of the furanone |

| NMR (CDCl$_3$ ; 250 MHz) | | |
|---|---|---|
| 3.77 | (m) | CH (—NH—CH(CH$_3$)(Ph)) |
| 4.96 | (d, J = 5) | CH at 5 of the furanone |
| 7.20 to 7.40 | (m) | 5H aromatic |

Stage 5: formation of the monochloroacetic acid salt of the cis diastereoisomer(4S,5R)
4(S) [4α(S*), 5α]-dihydro-5-ethoxy-4-[(1-phenylethyl)amino]-2(3H)-furanone chloroacetate 1.82 g of monochloroacetic acid (96%) are added, under an inert atmosphere, at 20–25° C., to 5 g of the cis diastereoisomer obtained in the above stage in 50 ml of tert-butyl methyl ether. A solution is obtained which crystallizes rapidly, and is left for 1 hour 30 min. at ±5° C. 5.75 g of the expected product are obtained.
m.p.=106–108° C.
[α$_D$]=−11°5 (c=1% CH$_3$OH)

Stage 6: hydrogenolysis
a) desalification (return to the free amine)
4(S)[4α(S*),5α]-dihydro-5-ethoxy-4-[(1-phenylethyl)amino]-2(3H)-furanone 5.55 g of the monochloroacetic salt obtained in the above stage, 60 ml of dichloromethane and 55 ml of sodium bicarbonate are mixed together at 0–5° C., under an inert atmosphere, and the mixture is stirred for 10 min., washed, extracted, dried and evaporated under reduced pressure to give 3.95 g of desalified product in the form of an oil.

b) Formation of the hydrochloride
4(S)[4α(S*),5α]-dihydro-5-ethoxy-4-[(1-phenylethyl)amino]-2(3H)-furanone hydrochloride 6.6 ml of 2N hydrochloric acid in isopropyl ether are added dropwise, at 0–5° C. to 3.36 g of the product obtained above in 66 ml of isopropyl ether, and the resulting solution is maintained for 1 hour at this temperature. Crystallization is observed. 3.77 g of the expected hydrochloride are obtained.

c) Hydrogenolysis
(4(S)-cis)-4-amino-5-ethoxydihydro-2(3H)-furanone hydrochloride 1.8 ml of water are added to a suspension of 4 g of the hydrochloride obtained above in 60 ml of tetrahydrofuran, in order to obtain a solution, followed by addition of 400 mg of 10% palladium-on-charcoal. The mixture is stirred under 1.5 bar of hydrogen for 18 hours at 27–28° C. After filtration and rinsing with a tetrahydrofuran/water mixture, the mixture is evaporated under reduced pressure. 2.54 g of the expected product are obtained.

| [α$_D$] = −96° (c = 1% CH$_3$OH) | | |
|---|---|---|
| 1.22 | (t) | CH$_2$CH$_3$ |
| 2.58 | (dd, J = 8 and 17.5) | |
| 2.70 | (dd, J = 8 and 17.5) | CH$_2$ at 3 of the furanone. |
| 4.14 | (dt, J = 5.5 and 8) | CH at 4 of the furanone |
| 3.61; 3.90 | (m) | CH$_2$CH$_3$ |
| 5.71 | (d, J = 5.5) | CH at 5 of the furanone |
| 8.69 | (bs) | 3H mobile |

Stage 7: Formation of the allyl carbamate
(2R-cis) 2-propenyl (2-ethoxytetrahydro-5-oxo-3-furanyl)-carbamate 3 ml of pyridine are added, at +5° C. under an inert atmosphere, to a mixture consisting of 2.4 g of the product obtained in the above stage, 50 ml of dichloromethane and 1.55 ml of allyl chloroformate, the resulting mixture is stirred for one hour at this temperature and 0.56 ml of allyl chloroformate and 1 ml of pyridine are then added. This mixture is stirred for 6 hours at room temperature, poured into water, extracted with dichloromethane, washed, dried and evaporated under reduced pressure to give 2.66 g of crude product, which product is recrystallized from isopropyl ether. 1.95 g of pure expected product are obtained.

| [α$_D$] = −56° (c = 1% CH$_2$Cl$_2$) | | |
|---|---|---|
| 1.26 | (t) | CH$_2$CH$_3$ |
| 2.47 | (dd, J = 10 and 17.5) | |
| 2.84 | (dd, J = 8.5 and 17.5) | CH$_2$ at 3 of the furanone |
| 3.67 | (dq) and 3.92 (dq) | CH$_2$CH$_3$ |
| 4.55 | (m) | CH at 4 of the furanone |
| 4.59 | (bd) | CH$_2$—CH=CH$_2$ |
| 5.45 | (d, J = 5.5) | CH at 5 of the furanone |
| 5.25 | (dq) and 5.33 (dq) | CH$_2$—CH=CH$_2$ |
| 5.30 | masked | N—H |
| 5.93 | (m) | CH$_2$—CH=CH$_2$ |

EXAMPLE 2

(2R-cis) 2-propenyl (2-ethoxytetrahydro-5-oxo-3-furanyl) carbamate

Stage 1: Michael Addition
4(S*) dihydro-5-ethoxy-4[(1-phenylethyl)amino]-2(3H)-furanone 15 ml of 98% S-(−)-phenylethylamine are added over 30 min between 23 and 25° C., under an inert atmosphere, to 15 g of racemic ethoxyfuranone in 75 ml of dimethylformamide, and the solution obtained is stirred for 24 hours and then poured into a water/ice mixture. After extraction with cyclohexane, washing and drying, the solution is evaporated under reduced pressure to give 26.6 g of an oil corresponding to an expected 45/55 mixture of the trans isomers.

| NMR (CDCl$_3$ ; 250 MHz) | | |
|---|---|---|
| 1.12 (t) ; 1.22 (t) | | CH$_2$CH$_3$ |
| 1.37 | (dd) | CH$_3$ (—NH—CH(CH$_3$) (Ph)) |
| 2.13 | (dd, J = 3.5 and 17.5) | |
| 2.35 | (dd, J = 3 and 127.5) | CH$_2$ at 3 of the furanone |
| 2.70 | (dd, J = 7.5 and 17.5) | |
| 2.80 | (dd, J = 7 and 17.5) | |
| 3.26 | (m) | CH at 4 of the furanone |
| 3.30 to 3.90 | (m) | CH$_2$CH$_3$ |
| 3.82 | (m) | CH (—NH—CH(CH$_3$)(Ph)) |
| 5.00 and 5.32 | (d, J = 1.5) (d, J = 1.5) | CH at 5 of the furanone |
| 7.2 to 7.4 | (m) | 5H aromatic |

Stage 2: Resolution of the Two Trans Diastereoisomers
a) production of the trans diastereoisomer (4R,5R)
4(R)[4α(S*),5β]-dihydro-5-ethoxy-4-[(1-phenylethyl)amino]-2(3H)-furanone trichloroacetate A solution of 10.24 g of trichloroacetic acid (99.5%) in 50 ml of tert-butyl ether is added over 30 min. to 26 g of the mixture from the above stage in 155 ml of tert-butyl ether. The solution obtained is stirred for 2 hours at 20–25° C. and then for 2 hours at 5° C. 12.63 g of the (4R,5R) isomer are obtained in the form of the trichloroacetic acid salt.

| $[\alpha_D]$ -72°5 (c = 1% CH$_3$OH) NMR (CDCl$_3$ ; 250 MHz) | | |
|---|---|---|
| 1.15 | (t) | CH$_2$CH$_3$ |
| 1.75 | (d, J = 7) | CH$_3$ (—NH—CH(CH$_3$) (Ph)) |
| 2.78 | (dd, J = 8.5 and 18.5) | |
| 3.05 | (dd, J = 4 and 18.5) | CH$_2$ at 3 of the furanone |
| 3.43 | (ddd, J = 2–4 and 8.5) | CH at 4 of the furanone |
| 3.59 | (dq, 1H) 3.79 (dq, 1H) | CH2CH3 |
| 4.29 | (q, J = 7) | (—NH—CH(CH$_3$) (Ph)) |
| 5.77 | (d, J = 1.5) | CH at 5 of the furanone |
| 7.42 to 7.57 | | 5H aromatic |
| 9.80 | (broad m) | H mobile | b) production of the trans diastereoisomer (4S,5S) 4(S)[4α(R*),5β]-dihydro-5-ethoxy-4-[(1-phenylethyl) amino]-2(3H)-furanone chloroacetate the mother liquors from the above stage are washed with saturated sodium bicarbonate solution and then re-extracted with tert-butyl ether. After drying, the solution is evaporated under reduced pressure to give 17.43 g of the expected product in the form of an oil. 130 ml of isopropanol are added, followed by 5 g of monochloroacetic acid, and the mixture is heated to 40° C. Dissolution and then crystallization are observed, after which the mixture is stirred for one hour at room temperature and then for two hours at 0–5° C. 12.48 g of the expected (4S,5S) isomer are obtained in the form of the monochloroacetic acid salt.

| $[\alpha_D]$ = +1° (c = 1% CH$_3$OH) NMR (CDCl$_3$ ; 250 MHz) | | |
|---|---|---|
| 1.12 | (t, J = 7.5) | CH$_2$CH$_3$ |
| 1.26 | (d, J = 6.5) | CH$_3$ (—NH—CH(CH$_3$) (Ph)) |
| 2.18 | (dd, J = 2.5 and 17.5) | |
| 2.66 | (dd, J = 7.5 and 17.5) | CH$_2$ at 3 of the furanon |
| 2.95 | (ddd, J = 1–2.5 and 7.5) | CH at 4 of the furanone |
| 3.66 | (m) | CH$_2$CH$_3$ |
| 3.87 | (q, J = 6.5) | CH (—NH—CH(CH$_3$) (Ph)) |
| 5.42 | (d, J = 1) | CH5 of the furanone |
| 7.24 | (m) 1H, 7.33 (m) 4H | H aromatic |
| 4.26 | (s) | X—CH$_2$ |

Stage 3: production of the desalified (4S,5S) compound 4(S)[4α(R*),5β]-dihydro-5-ethoxy-4-[(1-phenylethyl) amino]-2(3H)-furanone 12.35 g of the salt obtained in Stage 2B and 130 ml of dichloromethane are mixed together at 0–5° C., followed by addition of 100 ml of saturated sodium bicarbonate solution. After stirring for 10 min., the mixture is extracted, washed, dried and evaporated under reduced pressure to give 8.9 g of the desalified product.
$[\alpha_D]$=−6.6° (c=1% CH$_3$OH)

Stage 4: epimerization: production of the (4S,5R) diastereoisomer 4(S)[4α(R*),5α]-dihydro-5-ethoxy-4-[(1-phenylethyl) amino]-2(3H)-furanone 37 ml of 1M tin tetrachloride in dichloromethane are added, under an inert atmosphere over 45 minutes at 0–5° C., to 8.8 g of the desalified (4S,5S) compound obtained in Stage 3 in 175 ml of dichloromethane, and the resulting mixture is stirred for 1 hour at this temperature. 14.1 ml of acetic acid are then added, this mixture is stirred for 1 hour at 0–5° C., poured into a water/ice mixture and washed, cyclohexane is added, this mixture is brought to pH 7–8 by addition of sodium bicarbonate, and it is extracted with cyclohexane, dried and evaporated under reduced pressure to give 3.96 g of the expected product in the form of an oil corresponding to a 90/10 cis/trans ratio).

| NMR (CDCl$_3$ ; 250 MHz) | | |
|---|---|---|
| 1.29 | (t) | CH$_2$CH$_3$ |
| 1.35 | (d) | CH$_3$ (—NH—CH(CH$_3$) (Ph)) |
| 2.28 | (dd, J = 11.5 and 17) | |
| 2.43 | (dd, J = 8 and 17) | CH$_2$ at 3 of the furanone. |
| 3.36 | (ddd, J = 4.5/8/1.5) | CH at 4 of the furanone |
| 3.67 | (dq) ; 3.92 (dq) | CH$_2$CH$_3$ |
| 3.81 | (q) | CH (—NH—CH(CH$_3$) (Ph)) |
| 5.79 | (d, J = 4.5) | CH at 5 of the furanone |
| 7.20 to 7.40 | (m) | 5H aromatic |

Stare 5: formation of the trichloroacetic acid salt of the cis diastereoisomer (4S,5R) 4(S)[4α(R*),5β]-dihydro-5-ethoxy-4-[(1-phenylethyl) amino]-2(3H)-furanone trichloroacetate 2.34 g of trichloroacetic acid (99%) are added, under an inert atmosphere at 20–25° C., to 3.8 g of the cis diastereoisomer obtained in the above stage in 40 ml of tert-butyl methyl ether. The mixture is left for 1 hour at 0–5° C. to give 5.58 g of the expected product.
$[\alpha_D]$=−49° (c=0.9% CH$_3$OH)

Stage 6: hydrogenolysis
a) desalification (return to the free amine)
4(S)[4α(R*),5α]-dihydro-5-ethoxy-4-[(1-phenylethyl) amino]-2 (3H) -furanone 5.41 g of the trichloroacetic acid salt obtained in the above stage, 50 ml of cyclohexane and 50 ml of saturated sodium bicarbonate solution are mixed together at 0–5° C. under an inert atmosphere, the mixture is stirred until dissolved, and it is washed, extracted, dried and evaporated under reduced pressure to give 3.18 g of desalified product in the form of an oil.
$[\alpha_D]$=−93° (c=0.62% CH$_3$OH)

This product is re-purified by mixing 2.85 g of this product with 30 ml of cyclohexane and 2.8 g of silica for 10 min. After treatment, 2.3 g of a colourless oil are collected.
b) formation of the hydrochloride
4(S)[4α(R*),5α]-dihydro-5-ethoxy-4-[(1-phenylethyl) amino]-2(3H)-furanone hydrochloride 4 ml of 2N hydrochloric acid in isopropyl ether are added dropwise, at 0–5° C., to 2 g of the product obtained above in 40 ml of isopropyl ether, and the mixture is maintained for 15 minutes at this temperature. The mixture is evaporated under reduced pressure to give 2.29 g of the expected hydrochloride.
c) hydrogenolysis
(4(S) -cis) -4-amino-5-ethoxydihydro-2(3H)-furanone hydrochloride 1 ml of water and then 300 mg of 10% palladium-on-charcoal are added to a suspension of 2.29 g of the hydrochloride obtained above in 40 ml of tetrahydrofuran . The mixture is stirred under 1.5 bar of hydrogen for 5 hours. After filtration and rinsing with a tetrahydrofuran/water mixture, the resulting mixture is evaporated under reduced pressure at 45° C. 1.40 g of the expected product are obtained.

| $[\alpha_D]$ = −87°4 (c = 1% CH$_3$OH) | | |
|---|---|---|
| 1.22 | (t) | CH$_2$CH$_3$ |
| 2.58 | (dd, J = 8 and 1.5) | |

-continued

| [α_D] = −87°4 (c = 1% CH₃OH) | | |
|---|---|---|
| 2.70 | (dd, J = 8 and 17.5) | CH₂ at 3 of the furanone |
| 4.14 | (dt, J = 5.5 and 8) | CH at 4 of the furanone |
| 3.61 to 3.9 | (m) | CH₂CH₃ |
| 5.71 | (d, J = 5.5) | CH at 5 of the furanone |
| 8.69 | (bs) | 3H mobile |

Stage 7: Formation of the allyl carbamate (2R-cis) 2-propenyl (2-ethoxytetrahydro-5-oxo-3-furanyl)-carbamate 1 ml of 99% allyl chloroformate and then 2 ml of pyridine are added at +5° C., under an inert atmosphere, to 1.3 g of the product obtained in the above stage in 50 ml of dichloromethane, the mixture is stirred for 1 hour 40 min. at this temperature and 0.3 ml of allyl chloroformate and 0.6 ml of pyridine are then added. This mixture is stirred for 16 hours at room temperature, poured into water, extracted with dichloromethane, washed, dried and evaporated under reduced pressure to give 1.62 g of crude product, which product is recrystallized from isopropyl ether. 1.34 g of the expected product are obtained.

| [α_D] = −52.4° (c = 1% CH₂Cl₂) | | |
|---|---|---|
| 1.26 | (t) | CH₂CH₃ |
| 2.47 | (dd, J = 10 and 17.5) | |
| 2.84 | (dd, J = 8.5 and 17.5) | CH₂ at 3 of the furanone |
| 3.67 | (dq) and 3.92 (dq) | CH₂CH₃ |
| 4.55 | (m) | CH at 4 of the furanone |
| 4.59 | (bd) | CH₂—CH=CH₂ |
| 5.45 | (d, J = 5.5) | CH at 5 of the furanone |
| 5.25 | (dq) and 5.33 (dq) | CH₂—CH=CH₂ |
| 5.30 | masked | N—H |
| 5.93 | (m) | CH₂—CH=CH₂ |

EXAMPLE 3

4(S)[4α(S*),5α]-dihydro-5-ethoxy-4-[(1-phenylethyl)amino]-2(3H)-furanone dichloroacetate Stage 1: Michael Addition 4(R*) dihydro-5-ethoxy-4-[(1-phenylethyl)amino]-2(3H)-furanone 20 ml of R-(+)-1-phenylethylamine (19.06 g) are added over about 1 h 30 min., with stirring and under a nitrogen atmosphere, to a solution of 20 g of racemic ethoxyfuranone in 156.8 ml of isopropanol and 3.2 ml of water, while maintaining the temperature at 0±2° C., and the resulting mixture is stirred for 24 hours at this temperature.

Stage 2: resolution of the two trans diastereoisomers: production of the trans diastereoisomers (4S,5S)

4(S)[4α(S*),5β]-dihydro-5-ethoxy-4-[(1-phenylethyl)amino]-2(3H)-furanone trichloroacetate A solution consisting of 25.55 g of trichloroacetic acid in 39.2 ml of isopropanol and 0.8 ml of demineralized water is added to the above solution (the product is not isolated), the temperature is allowed to rise to 20–22° C., and crystallization of the salt is observed after the end of the introduction. This suspension is maintained for 24 hours at 20–22° C., and the product is then spin-dried and washed with isopropanol containing 2% water. 18 g of the expected product are obtained.

| 1.15 | (t) | O—CH₂—CH₃ |
|---|---|---|
| 1.75 | (d, J = 7) | Ph—CH(CH₃)—N |
| 2.78 | (dd, J = 8.5 and 18.5) | CH₂ at 3 |
| 3.05 | (dd, J = 4 and 18.5) | |
| 3.43 | (ddd, J = 2.4 and 8.5) | H₄ |
| 3.59 | (dq) 1H, 3.79 (dq) 1H | O—CH₂—CH₃ |
| 4.29 | (q, J = 7) | Ph—CH(CH₃)—N |
| 5.77 | (d, J = 1.5) | H5 |
| 7.42 to 7.57 | (5H) | H aromatic |
| 9.80 | broad | H mobile. |

Stage 3: epimerization: production of the (4S,5R) diastereoisomer

4(S)[4α(S*),5α]-dihydro-5-ethoxy-4-[(1-phenylethyl)amino]-2(3H)-furanone 45 ml of methanesulphonic acid are added, under nitrogen, while maintaining the temperature at 20±2° C., to a suspension of 50 g of the (4S,5S) trichloroacetate obtained in the above stage in 150 ml of toluene, the mixture is maintained for 2 hours at 20±2° C. and, after lowering the temperature to 0±5° C., 111 ml of triethylamine are added over 1 h 30 min. After a series of washing, extraction and drying, 400 ml of a solution containing an 85/15 mixture of cis/trans isomer are obtained.

Stage 4: formation of the dichloroacetic acid salt of the cis (4S,5R) diastereoisomer 4(S)[4α(S*),5α]-dihydro-5-ethoxy-4-[(1-phenylethyl)amino]-2(3H)-furanone dichloroacetate 10 ml of dichloroacetic acid are added to 400 ml of the above solution, this mixture is concentrated to 6 volumes, crystallization is observed, and stirring is maintained at 20=2 C for 2 hours under nitrogen. After washing with toluene, 32.8 g of the expected product are obtained.

| 1.21 | (t) | O—CH₂—CH₃ |
|---|---|---|
| 1.72 | (d, J = 6.5) | Ph—CH(CH₃)—N |
| 2.77 | (dd, J = 8.5 and 17) | CH₂ at 3 |
| 2.97 | (dd, J = 11 and 17) | |
| 3.76 | (m) | H₄ |
| 3.34 | (dq), 3.66 (dq) | O—CH₂—CH₃ |
| 4.27 | (q, J = 6.5) | Ph—CH(CH₃)—N |
| 4.88 | (d, J = 5) | H₅ |
| 5.95 | (s) | CHCl₂ |
| 7.42 | (m) 3H, 7.51 (m) 2H | H aromatic. |
| 9.79 | (bs) | 2H mobile. |

What is claimed is:

1. A compound selected from the group consisting of a compound of the formula

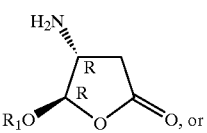

IVa

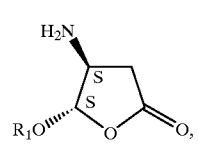

IVb

-continued

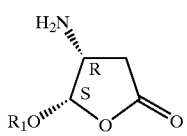
IVc

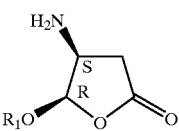
IVd wherein $R_1$ is alkyl of 1 to 4 carbon atoms or phenylalkyl of 7 to 11 carbon atoms or their acid addition salts.

2. A compound of claim 1 of the formula

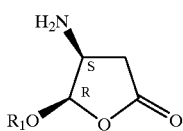
IVd and its acid addition salts.

3. The compound of claim 2 wherein $R_1$ is ethyl and its acid addition salts.

4. A process for the preparation of a compound of claim 1 comprising a) reacting an arylamine of the formula $R_3$—$R_4$CH—$NH_2$ wherein $R_3$ is hydrogen or alkyl of 1 to 4 carbon atoms and $R_4$ is aryl with a racemic alkoxyfuranone of the formula

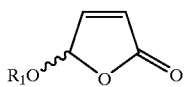
II wherein $R_1$ is alkyl of 1 to 4 carbon atoms or phenylalkyl of 7 to 11 carbon atoms to produce the trans isomer (4R,5R) and (4S, 5S) of the formulae

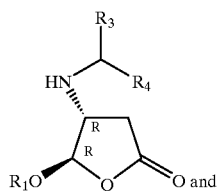
IIIa

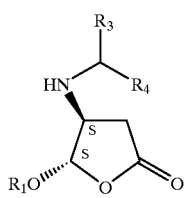
IIIb and separating the isomers by crystallization and optionally salification or when $R_3$ is hydrogen, by resolution with an optically active acid
b) optionally subjecting a compound of Formulae IIIA or IIIb in the presence of an acid to epimerization to obtain the cis isomers (4R,5S) or (4S,5R) of the formulae

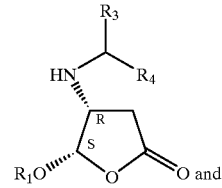
IIIc

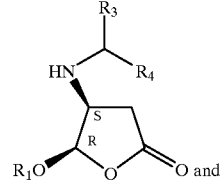
IIId c) subjecting to hydrolysis the trans isomer (4R,5R) or (4S,5S) of Formulae IIIa or IIIb to obtain the trans isomer (4R, 5R) or (4S, 5S) of compounds of Formulae IVa or IVb or the cis isomer of (4R, 5S) or (4S, 5R) of Formulae IIIc or IIId to obtain the cis isomer (4R,5S) or (4S,5R) of Formulae IVc or IVd compounds of Formulae IVa, IVb, IVc or IVd being optionally salified and/or protected.

5. The process of claim 4 wherein the compounds of Formulae IVa, Ib, IVc or IVd are reacted with a compound of the formula $R_2$ $CH_2$—O—CO—Cl wherein $R_2$ is selected from the group consisting of tert-butyl, alkenyl of 2 to 4 carbon atoms, alkynyl of 2 to 4 carbon atoms and phenyl to obtain the trans (4R, 5R) or (4S,5S) diastereoisomers or the cis (4R,5S) or (4S,5R) diastereoisomers of compounds of the formulae

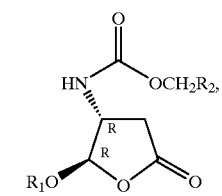
Ia

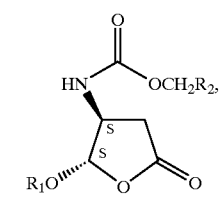
Ib

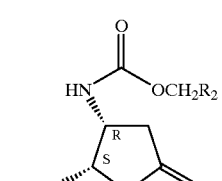
Ic

-continued

Id

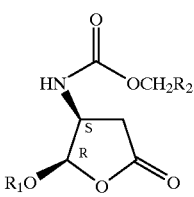

and optionally salifying the same.

6. The process of claim 5 where the compounds of Formulae IIIa and IIIb are separated by crystallization by reaction with trichloroacetic acid and then with monocloroacetic acid on the mother liquors to obtain the other diastereoisomer of IIIa or IIIb.

7. The process of claim 4 to form a compound of the formulae

IVd

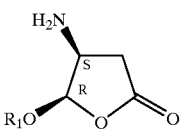

or the compound of the formula

Id

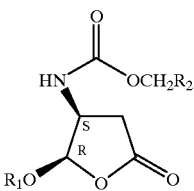

comprising a) reacting R phenylethylamine with a compound of the formula

II

to obtain a compound of the formula

III'a

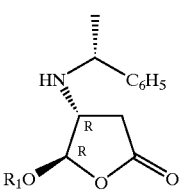

-continued

III'b

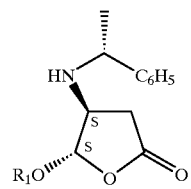

b) reacting the latter compounds with trichloroacetic acid to form the said salt of the (4S, 5S) stereoisomer of Formula III'b followed by reaction of the mother liquor with monochloroacetic acid to the said salt of the (4R,5R) stereoisomer of formula III'a c) optionally reacting the salts with a base to form the free amines d) subjecting the (4S, 5S) stereoisomer of Formula III'b to epimerization in the presence of an acid to obtain the cis (4S, 5R) stereoisomer of the Formula III'd

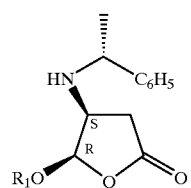

e) optionally reacting the latter with monochloroacetic acid or dichloroacetic acid for crystallization and optionally treating the same with a base to form the free amine optionally resalified in the form of the hydrochloride f) subjecting the cis (4S, 5R) stereoisomer of Formula III'd to hydrogenolysis to form the cis (4S, 5R) stereoisomer of Formula IVd g) optionally reacting the latter with allyl chloroformate to obtain the cis (4S,5R) stereoisomer of Formula Id wherein $R_2$ is —CH=CH$_2$.

8. The process of claim 4 for the preparation of a compound of the Formula

IVd

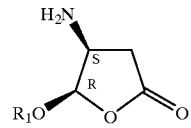

or a compound of the formula

Id

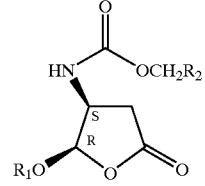

comprising a) reacting a compound of Formula II with S phenylethylamine to form a compound of the formulae

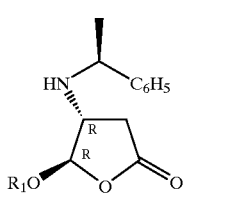

III″a

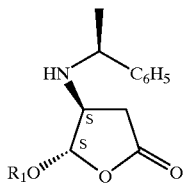

III″b b) reacting the latter compounds with trichloroacetic acid to form the acid salt of the (4R,5R) stereoisomer of Formula III″a and reacting the mother liquor with monochloroacetic acid to form the acid salt of the (4S,5S) stereoisomer of Formula III″b and optionally reacting the same with a base to form the free amine c) subjecting the (4S,5S) stereoisomer of Formula III″b to epimerization in the presence of an acid to obtain the cis (4S, 5R) stereoisomer of the Formula

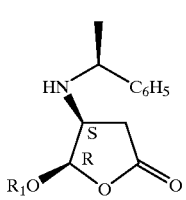

III″d d) optionally reacting the latter with dichloroacetic acid or monochloroacetic acid for crystalline and optionally reacting the latter with a base to form the free amine and optionally resalified in the form of the hydrochloride e) subjecting the cis (4S,5R) stereoisomer to hydrogenolysis to form the cis (4S,5R) stereoisomer of Formula IVd f) optionally reacting the latter with allyl chloroformate to form the cis (4S,5R) diastereoisomer of Formula Id where $R_2$ is CH—$CH_2$.

9. The process of claim 4 wherein the reaction with the amine of Formula II is effected in dimethylformamide or aqueous isopropanol.

10. The process of claim 4 wherein the epimerization is effected with the tetrachloride or methane sulfonic acid.

11. The process of claim 4 wherein $R_1$ is ethyl.

12. The process if claim 4 wherein the resolution is effected with trichloroacetic acid in aqueous isopropanol.

13. The process of claim 4 wherein the epimerization is effected with methanesulfonic acid in toluene.

14. The process of claim 4 wherein the crystallization is effected with dichloroacetic acid in toluene.

15. Process as defined in claim 8, characterized in that the resolution of the trans stereoisomers with trichloroacetic acid (step b) is carried out in aqueous isopropanol.

16. A compound having the formula selected from the group consisting of

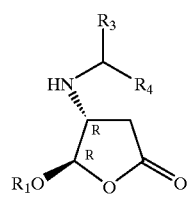

IIIa

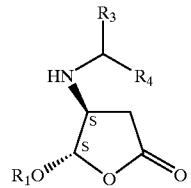

IIIb

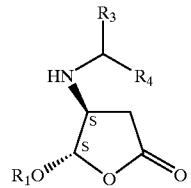

IIIc

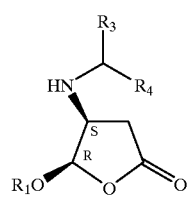

IIId wherein $R_1$ is alkyl of 1 to 4 carbon atoms or phenylalkyl of 7 to 11 carbon atoms, $R_3$ is hydrogen or alkyl of 1 to 4 carbon atoms and $R_4$ is aryl and their acid addition salts with the exception of the compounds of the Formula

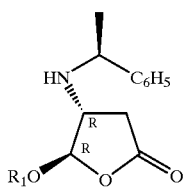

III″a

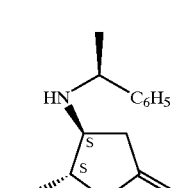

III″b

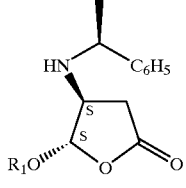

wherein $R_1$ is methyl.

17. The process of claim 7 wherein the resolution of the trans stereoisomers with trichloroacetic acid (step b) is carried out in aqueous isopropanol.

* * * * *